US012661015B2

(12) United States Patent
Mukkamala et al.

(10) Patent No.: US 12,661,015 B2
(45) Date of Patent: Jun. 23, 2026

(54) TECHNIQUES FOR SCREENING AND MONITORING PATIENTS FOR AORTIC ANEURYSMS

(71) Applicants: Board of Trustees of Michigan State University, East Lansing, MI (US); University of Maryland, College Park, MD (US)

(72) Inventors: Ramakrishna Mukkamala, Okemos, MI (US); Mohammad Yavarimanesh, Lansing, MI (US); Jin-Oh Hahn, Rockville, MD (US)

(73) Assignees: Board of Trustees of Michigan State University, East Lansing, MI (US); University of Maryland, College Park, MD (US)

( * ) Notice: Subject to any disclaimer, the term of this patent is extended or adjusted under 35 U.S.C. 154(b) by 515 days.

(21) Appl. No.: 18/016,533

(22) PCT Filed: Jul. 16, 2021

(86) PCT No.: PCT/US2021/042051
    § 371 (c)(1),
    (2) Date: Jan. 17, 2023

(87) PCT Pub. No.: WO2022/016103
    PCT Pub. Date: Jan. 20, 2022

(65) Prior Publication Data
    US 2023/0270343 A1     Aug. 31, 2023

Related U.S. Application Data

(60) Provisional application No. 63/053,001, filed on Jul. 17, 2020.

(51) Int. Cl.
    *A61B 5/0295*     (2006.01)
    *A61B 5/00*     (2006.01)
    (Continued)

(52) U.S. Cl.
    CPC ........ *A61B 5/02014* (2013.01); *A61B 5/0261* (2013.01); *A61B 5/0295* (2013.01);
    (Continued)

(58) Field of Classification Search
    CPC ........ G16H 50/20; A61B 5/7267; A61B 8/06; A61B 5/026; A61B 5/02007; A61B 5/318;
    (Continued)

(56) References Cited

U.S. PATENT DOCUMENTS 6,819,950 B2 *  11/2004  Mills ................. A61B 5/14551
                                                          600/323
2013/0116576 A1   5/2013  Morren
                       (Continued)

FOREIGN PATENT DOCUMENTS

KR     20150016903 A     2/2015
WO     WO-03039326 A2     5/2003

OTHER PUBLICATIONS

International Search Report and Written Opinion of the ISA issued in PCT/US2021/042051, mailed Nov. 3, 2021; ISA/US, 9 pages.

*Primary Examiner* — Deborah L Malamud
(74) *Attorney, Agent, or Firm* — Harness, Dickey and Pierce

(57) ABSTRACT

An aortic aneurysm carries increasing risk of rupture with growing aneurysm diameter. This condition is typically asymptomatic, so screening and surveillance are essential. Ultrasound and other imaging methods are employed for such monitoring at high accuracy. However, these methods require an expert and are expensive. Aortic aneurysms are considerably under-detected at present and may become even more under-detected in the future as the disease prevalence increases with societal aging. This disclosure present (Continued)

devices that are convenient in use and cost for aortic aneurysm screening and surveillance.

8 Claims, 3 Drawing Sheets

(51) Int. Cl.

| | |
|---|---|
| *A61B 5/02* | (2006.01) |
| *A61B 5/026* | (2006.01) |
| *A61B 5/11* | (2006.01) |

(52) U.S. Cl.
CPC .......... *A61B 5/1102* (2013.01); *A61B 5/6898* (2013.01); *A61B 5/7282* (2013.01)

(58) Field of Classification Search
CPC ... A61B 5/02028; A61B 5/0205; A61B 5/021; A61B 5/024; A61B 5/486; A61B 5/0295; A61B 5/7275; A61B 5/02108; A61B 5/72; A61B 5/0245; A61B 5/74; A61B 5/0285
See application file for complete search history.

(56) References Cited

U.S. PATENT DOCUMENTS

| | | |
|---|---|---|
| 2015/0323311 A1 | 11/2015 | Muijs et al. |
| 2017/0020435 A1 | 1/2017 | Lovoi et al. |
| 2019/0216340 A1 | 7/2019 | Holz et al. |

* cited by examiner

Measure Arterial
Waveform — 11

Extract Features — 12

Detect Aneurysm — 13

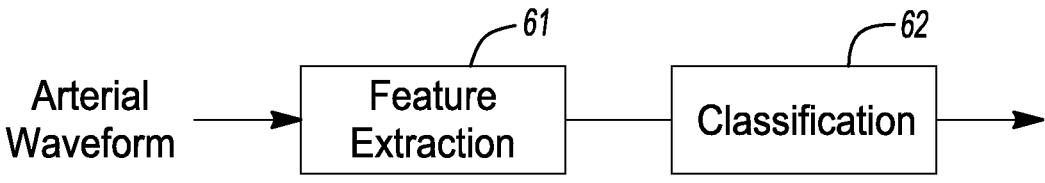
_Fig-6_
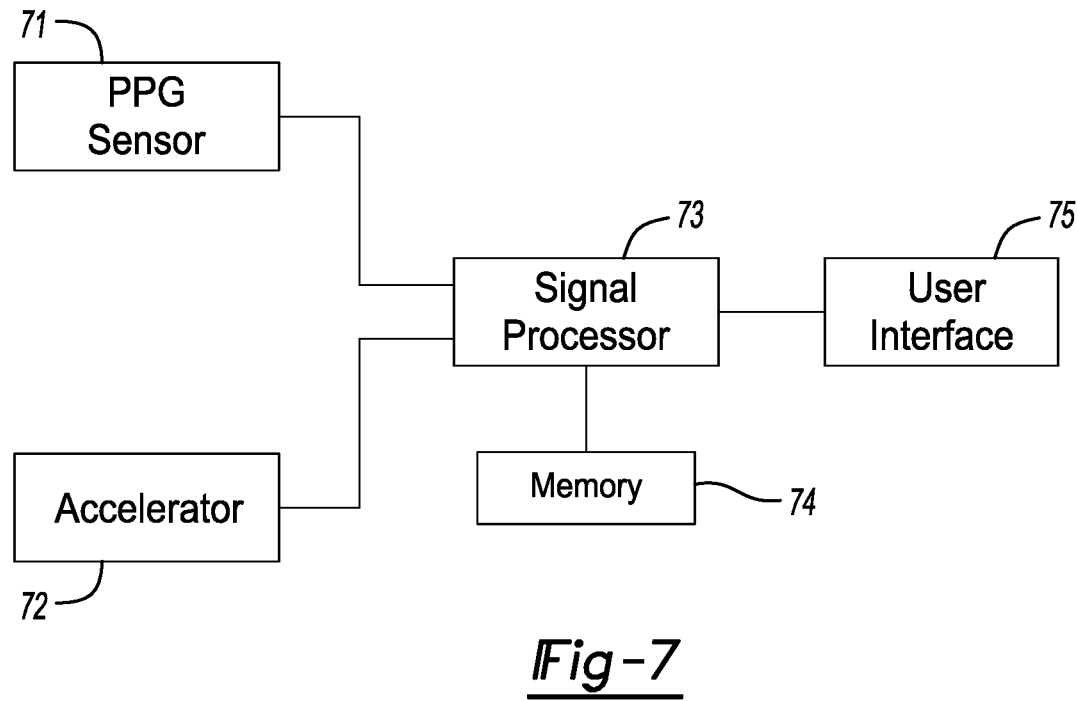
_Fig-7_

TECHNIQUES FOR SCREENING AND MONITORING PATIENTS FOR AORTIC ANEURYSMS

CROSS-REFERENCE TO RELATED APPLICATIONS

This application is a 371 U.S. National Phase of International Application No. PCT/US2021/042051, filed Jul. 16, 2021, which claims the benefit of U.S. Provisional Patent Application Ser. No. 63/053,001, filed on Jul. 17, 2020, which are incorporated by reference herein.

GOVERNMENT CLAUSE

This invention was made with government support under HL146470 awarded by the National Institutes of Health. The government has certain rights in the invention.

FIELD

The present disclosure relates to improved techniques for screening and monitoring patients for aortic aneurysms.

BACKGROUND

An aortic aneurysm is a balloon-like bulge in the main artery supplying blood to the body. In this condition, a weakened aortic wall in concert with the distending blood pressure causes progressive vessel expansion and, in some cases, rupture. A ruptured aorta has a mortality rate of approximately 80%.

Aneurysms are more common in the abdominal aorta than the thoracic aorta. An abdominal aortic aneurysm (AAA) is often defined as a vessel segment >3.0 cm in diameter. About 1% of men between 55 and 64 years of age have AAAs >4.0 cm in diameter, which have risk for rupture, and the prevalence of such clinically significant abdominal aortic aneurysms increases by 2-4% per decade thereafter. In women, abdominal aortic aneurysm are 4-6 times less common but may be 2-4 times more likely to rupture. In addition to male gender and advanced age, other abdominal aortic aneurysm risk factors include smoking history, family history, atherosclerosis, and hypertension. Abdominal aortic aneurysm is a top 15 leading cause of death in the United States. While the prevalence of abdominal aortic aneurysms may have recently declined likely due to a reduction in smoking, the future occurrence of abdominal aortic aneurysms could increase substantially as society ages.

Abdominal aortic aneurysms as well as thoracic aortic aneurysms (TAAs) can be accurately diagnosed with imaging methods operated by an expert. Ultrasound is preferred, because it has high sensitivity (94-100%) and specificity (98-100%) and is safe and lower in cost. Aortic aneurysms can be treated via surgery, either open or endovascular repair. The mortality rate of the surgical repair can be just 2-3%. Surgery is recommended for abdominal aortic aneurysms >5.5 cm in diameter or expanding at a rate >1 cm in diameter/year. Since most aortic aneurysms are asymptomatic, screening and surveillance are essential.

Aortic aneurysm diagnoses are often made based on incidental findings when imaging for other purposes, although a few advanced nations have created screening and surveillance programs. Based on a clinical benefit-harm analysis, the US Preventive Services Task Force (USPSTF) recommends one-time ultrasound screening for abdominal aortic aneurysm in all men aged 65 to 75 years who have ever smoked and in select men of the same age who have never smoked and suggests surveillance in patients with smaller abdominal aortic aneurysm ("e.g., ultrasound every 3-12 months"). However, the USPSTF notes that cost (e.g., ~$100 per ultrasound scan) must also be considered. Medicare covers one-time screening for adults with a family history of abdominal aortic aneurysm or men aged 65 to 75 years who have ever smoked. For comparison, England offers one-time ultrasound screening for all men after they turn 65 years of age. However, ultrasound is underutilized for abdominal aortic aneurysm screening in the range of <1-20% relative to the USPSTF guidelines, and poor patients are unduly under-screened. About 1.3 years of life are gained per 10 patients screened for abdominal aortic aneurysms, which is similar to breast cancer screening, so more abdominal aortic aneurysm screening could have major impact. Ultrasound may likewise be underutilized for abdominal aortic aneurysm surveillance. The USPSTF guidelines also assume fixed abdominal aortic aneurysm expansion rates, but abdominal aortic aneurysms can grow in spurts and even shrink over time. In addition, the USPSTF guidelines are based on the argument that competing causes of death are significant at very old ages (e.g., >80 years). However, this argument may become less tenable as society ages. Hence, other high-risk cohorts such as women who have ever smoked and very old men may also receive a net benefit from abdominal aortic aneurysm screening.

More convenient tools for screening and surveillance of aortic aneurysms would thus be a useful adjunct to ultrasound. However, physical exam via abdominal aortic palpation requires skill and is unreliable when the aneurysm is not large or the patient is not thin, and thoracic aortic palpation is not feasible due to the ribcage. As a result, key opinion leaders are now calling for point-of-care devices to foster more frequent aortic aneurysm monitoring.

This section provides background information related to the present disclosure which is not necessarily prior art.

SUMMARY

This section provides a general summary of the disclosure, and is not a comprehensive disclosure of its full scope or all of its features.

A method is presented for screening for aortic aneurysms in a subject. The method includes: measuring, by a sensor, at least one arterial waveform in a subject; extracting, by a signal processor, features from the at least one arterial waveform; and detecting, by the signal processor, an aortic aneurysm using the extracted features. The sensor may reside in a mobile phone or another portable computing device.

For example, pulse wave velocity may be extracted from the arterial waveform and an aortic aneurysm is detected based in part on a decrease in the pulse wave velocity of the subject. Additionally, the pulse wave velocity can be divided by blood pressure; and the presence of an aortic aneurysm is detected when a quotient of the pulse wave velocity divided by the blood pressure is less than a threshold.

In one embodiment, a waveform indicative of blood volume is measured using a photo-plethysmography (PPG) sensor.

In another embodiment, a ballistocardiography waveform is measured using an accelerometer or a weighing scale.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 6 is a block diagram showing components of a machine learning system.

FIG. 7 is a block diagram showing components of an example point-of-care device.

Corresponding reference numerals indicate corresponding parts throughout the several views of the drawings.

DETAILED DESCRIPTION

Example embodiments will now be described more fully with reference to the accompanying drawings.

Figures 1, 2, 3:
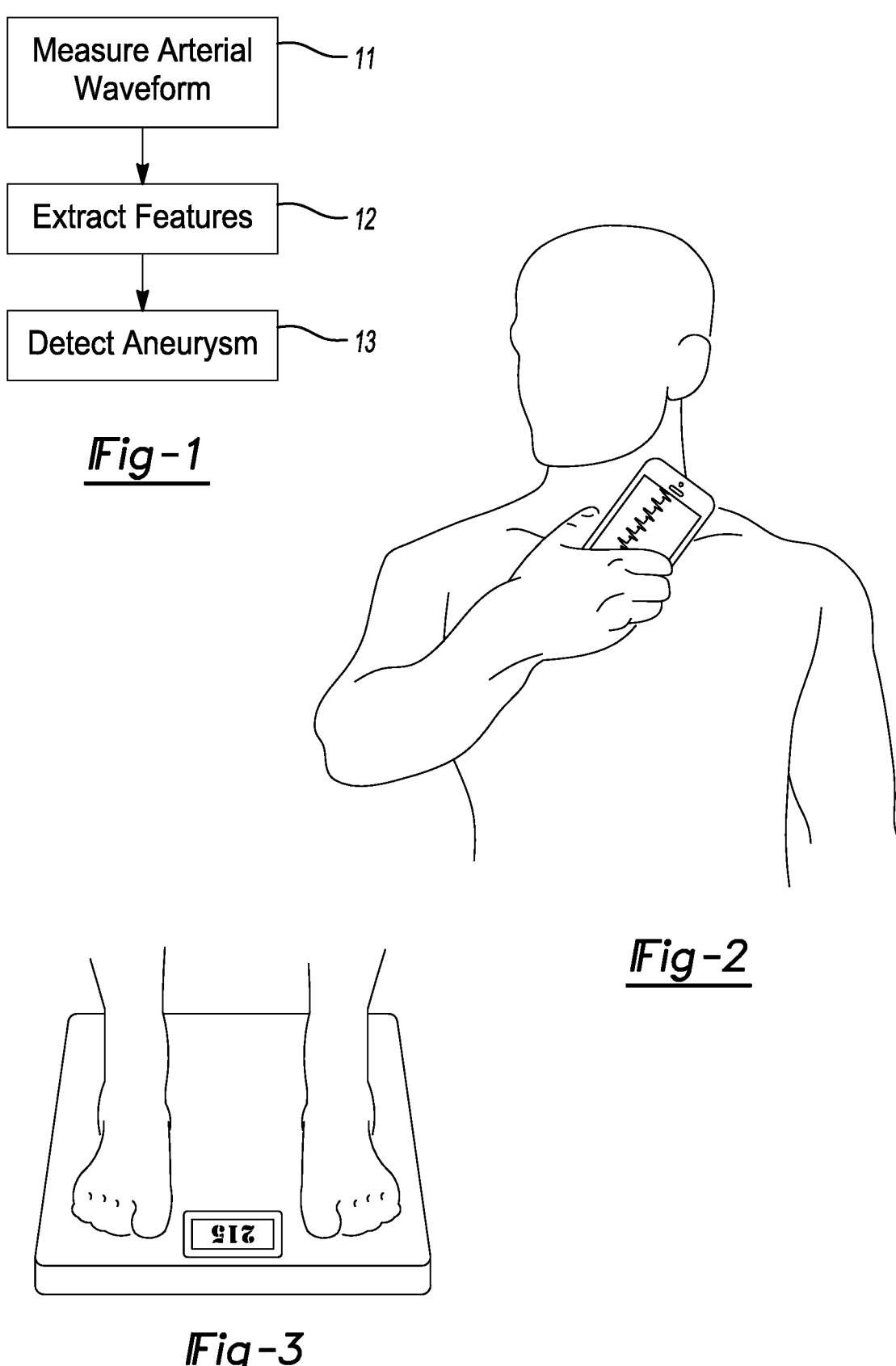
FIG. 1 is a flowchart providing an overview of a method for screening and/or monitoring aortic aneurysms in a subject.
FIG. 2 is a diagram of a subject using a mobile phone to measure arterial waveforms in the subject.
FIG. 3 is a diagram of a subject using a weighing scale to measure arterial waveforms in the subject.

FIG. 1 provides an overview of a method for screening and/or monitoring aortic aneurysms in a subject. The hallmark change of an aortic aneurysm is an increase in vessel diameter (d). Mechanical testing of ex vivo aortic walls suggests that the elastic modulus (E) also increases at the aneurysm. However, an aneurysm may have little effect on average aortic wall thickness (h). Hence, according to the well-known Moens-Korteweg equation ($PWV = \sqrt{(Eh/dp)}$), where p is blood density), if d increases more than E, pulse wave velocity (PWV) should decrease with aneurysm growth. On the other hand, E and thus PWV are also known to increase with blood pressure and age. Indeed, aortic PWV (normalized for BP) is lower in aortic aneurysm patients than age- and gender-matched controls and increases in patients after endovascular aneurysm repair (EVAR) to control values. Pulse wave velocity can be measured via the relative timing (foot-to-foot time delay) between proximal and distal arterial waveforms.

Normally, the main reflection sites in the arterial system are at the level of the arterioles due to the abrupt change in vessel diameter at this level. Since the diameter is decreasing (i.e., vessel tapering), the reflection coefficient and thus the reflected wave are positive. However, if an aortic aneurysm were present, the vessel diameter becomes larger at some distance from the heart. The increased diameter causes an appreciable negative reflection coefficient and reflected wave at this particular site. Hence, arterial waveforms should differ in shape in the presence of an aortic aneurysm due to the negative wave reflection from the aneurysm site on top of the positive wave reflection from the arterioles. Indeed, undulations in the blood pressure waveform, both proximal and distal to an aortic aneurysm, are apparent and then disappear after aneurysm repair. Wave separation confirms that the undulations are due to negative wave reflection by the aortic aneurysm.

To monitor an aortic aneurysm, arterial waveforms are measured and/or obtained at 11 using non-imaging sensors integrated into or commonly found in convenient point-of-care devices. In one example, arterial waveforms can be measured by a pulse oximeter or a photo-plethysmography (PPG) sensor. Such PPG sensors are commonly found in mobile phones (i.e., cameras) and can be used for measurement on the neck of the subject as seen in FIG. 2. In another example, an existing accelerometer in mobile phones, an accelerometer integrated into a point-of-care device, or a sensitive weighing scale as seen in FIG. 3 can be used to determine pulse wave velocity (PWV). More specifically, a time interval (e.g., IJ interval) of a ballistocardiogram is measured with the scale or an analogous interval of the ballistocardiogram is measured by the accelerometer, where the intervals indicate the pulse transit time (PTT). Alternatively, the scale could be integrated with a PPG sensor or electrical bioimpedance sensor on its surface to measure the distal waveform and pulse transit time could be detected as the time interval between the I-wave of the ballistocardiogram and the foot of the PPG/electrical bioimpedance waveform or another fiducial marker of the distal waveform. The pulse wave velocity is then derived by dividing the distance traveled by the pulse transit time. These examples are merely illustrative. Other types of arterial waveforms are envisioned by this disclosure. Likewise, other techniques for measuring such arterial waveforms also fall within the scope of this disclosure.

Aortic aneurysm growth alters the wave transmission and reflection characteristics and thus the observed arterial waveform. Features of the arterial waveform are thus extracted from the waveform as indicated at 12. In one example embodiment, a ratio of the pulse wave velocity to diastolic blood pressure is indicative of the size of an aortic aneurysm. Pulse wave velocity can be detected, for example at the level of diastolic blood pressure via the foot-to-foot time delay between the carotid and femoral or dorsal pedal waveforms. Pulse wave velocity decreases with increasing aneurysm diameter per the Moens-Korteweg equation but also decreases with decreasing blood pressure due to the nonlinear properties of the arterial wall. Thus, the ratio of the pulse wave velocity to diastolic blood pressure is a good indicator of the size of the aneurysm. Other techniques for determining pulse wave velocity are also envisioned by this disclosure.

Figures 4, 5:
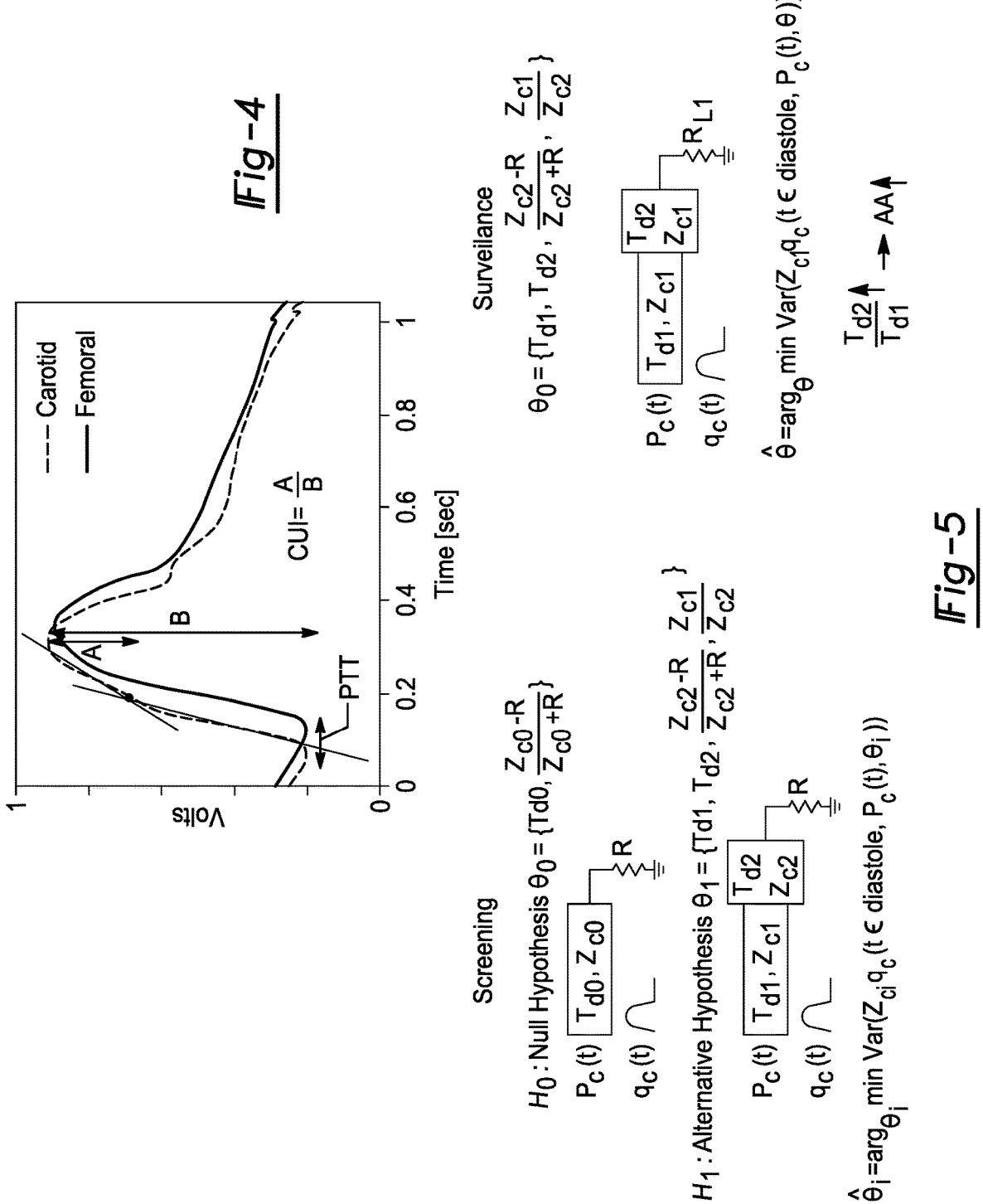
FIG. 4 is graph showing example features extracted from arterial waveforms.
FIG. 5 is a diagram showing example features extracted from arterial waveforms that is based on a physiologic model of arterial wave transmission and reflection.

In another embodiment, a feature indicative of shape of the arterial waveform during an upstroke of the arterial waveform correlates to the size of an aortic aneurysm. For example, a carotid waveform upstroke (CUI) feature is based on the presence of an early, negative wave reflection in the aortic aneurysm condition and may increase with increasing aneurysm diameter. This feature was obtained from two lines optimally fitted to the carotid waveform as seen in FIG. 4. In particular, the carotid upstroke feature is determined by identifying an intersection of two lines fitted to an upstroke of the arterial waveform, determining a first value measured between a peak of the arterial waveform and the intersection; determining a second value measured between the peak of the arterial waveform and the minimum of the at least one arterial waveform; and then computing a ratio of the first value to the second value. This ratio can serve as the carotid waveform upstroke feature. Other features indicative of the shape of the arterial waveform during an upstroke of the arterial waveform can also be used as indicators for the size of an aneurysm. For example, the time interval between the foot of the waveform and intersection divided by the time interval between the foot and peak of the waveform may be used.

As proof of concept, these two example features were tested using an existing patient database. The database included carotid and femoral artery tonometry waveforms, the physical distance between the carotid and femoral arteries (D), and arm cuff blood pressure (BP) values from thirty-nine (39) anonymized abdominal aortic aneurysm patients before and three weeks after endovascular repair (EVAR). In twenty (20) of these patients, the same measurements were also available three years after endovascular repair. The patients were old (75±10 years) and mostly male (95%) and many had comorbidities (e.g., hypertension) and were on medications (e.g., beta-blockers).

The two features were evaluated in terms of their abilities to classify pre-versus three weeks post endovascular repair and change from pre- to three weeks post endovascular repair versus change from 3 weeks to three years post endovascular repair. Receiver operating characteristic area under the curve was used as the quantitative metric of classification performance. Table 1 below illustrates the receiver operating characteristic area under the curve values for the two features.

TABLE 1

| Classification Results. | | |
|---|---|---|
| ROC AUC | PWV/BP | CUI |
| Pre- vs. 3 weeks post-EVAR (N = 39) | 0.77 | 0.72 |
| Change from pre- to 3 weeks post-EVAR vs. change from 3 weeks to 3 years post-EVAR (N = 20) | 0.75 | 0.80 |

The two features showed 72-80% accuracy for both classification tasks. These findings suggest that a convenient, non-imaging device can be more effective than aortic palpation in indicating whether an ultrasound is needed or not.

Continuing with reference to FIG. 1, the presence of an aortic aneurysm in the subject can be detected at 13 using the feature(s) extracted from the arterial waveform. For example, the PWV/BP ratio can be compared to a predetermined threshold and an aneurysm is deemed present when the value of the PWV/BP ratio falls below the predetermined threshold. The PWV/(BP*age) feature could also be used to account for PWV increases with aging. Similarly, the carotid waveform upstroke feature can be compared to a predetermined threshold and an aneurysm is deemed present when the value of the carotid waveform upstroke feature exceeds the threshold.

Alternatively or additionally, the size of an aortic aneurysm can be monitored over time. Rather than detecting the presence of an aortic aneurysm, the extracted features for a subject can be used to predict the size of the aneurysm via some model such as a multiple linear regression model. In either case, if the presence of an aneurysm is detected or the size of the aneurysm exceeds some threshold, additional steps may be taken to diagnosis the subject. Typically, the subject would undergo an ultrasound to confirm the diagnosis.

In another aspect, physic-based methods are used to extract features from the arterial waveform. For example, an arterial tube-load model is fit to the arterial waveforms to extract parameters indicative of aneurysm size. In general, two waveforms (an input and an output) are required for parameter estimation. In some instances, only one waveform can suffice by invoking the fact that the aortic blood flow rate waveform is zero during diastole or that aortic blood pressure decays smoothly. FIG. 5 shows a simplified modeling approach using two different models. One model assumes that an aortic aneurysm is absent and consists of a single tube with constant characteristic impedance [Zco] and supporting constant wave travel time [Td0], terminated by a resistance [R] for peripheral wave reflection. A second alternate model is comprised of two tubes in cascade and terminated by a resistance, where one tube denoted the normal aortic segment [Zc1, Td1] and the other tube defines the aneurysm segment [Zc2, Td2]. Both models are fit to the arterial waveform. If the latter model fits the arterial waveforms significantly better, then an aneurysm is present; otherwise, an absence of an aneurysm is presumed.

For surveillance of a known aneurysm, the second model is fit to the arterial waveform. Because Td1 and Td2 should be similarly impacted by age and blood pressure, the ratio of Td2/Td1 can be considered a specific index that increases with aneurysm size. It is envisioned that a reference measurement of the aneurysm size via imaging (i.e., training data) can be used to optimize the model complexity and the parameter estimation procedure (e.g., least square versus least absolute error). These models are merely exemplary. Other physics-based models also fall within the scope of this disclosure.

In yet another aspect, machine learning is used to extract and identify candidate features from the arterial waveforms. The features may be extracted automatically via deep learning (e.g., convolutional neural nets) if enough training data are available or manually using physiologic knowledge. Such features include pulse pressure (i.e., systolic blood pressure minus diastolic blood pressure), systolic or diastolic blood pressure, high frequency power and a number of local waveform maxima, ankle-brachial index for a measure of confounding peripheral arterial disease, pulse wave velocity, carotid waveform upstroke index, parameters from the physics-based method, although other features are contemplated by this disclosure. A feature vector comprised of one or more of these features may further include elements for demographic data for patients. A small number of impactful features may be derived using dimensionality reduction such as principal components analysis. Step-wise linear regression with the reference aneurysm diameter as a dependent variable may be used to select the candidate features. A multilayer perceptron or radial basis function net could be used starting with a single hidden layer. A linear activation function may be employed in the output layer and sigmoid or leaky rectified linear activation functions may be used in the hidden layer. Back propagation via the Levenberg-Marquardt algorithm may be applied for network training. The network depth may be increased as necessary and the hyperparameters may be determined by using a portion of the training set as a validation set or employing a cost function with regularization for number of parameters (e.g., weight decay, minimum description length (MDL), or Akaike Information Criterion (AIC)) to avoid reducing the training set.

Again, it may not be necessary to predict the aneurysm size. Classification of presence versus absence of aortic aneurysm and stable versus growing aneurysm may also be useful and performed using standard methods for multiple feature inputs such as binary logistic regression, support vector machines, neural networks etc. The features may be compared over time to classify stable versus growing aneurysm. With reference to FIG. 6, features are first extracted from the arterial waveform measured from the subject and used to construct a feature vector as indicated at 61. The feature vector is in turn classified at 62 using a classifier.

Prior to any waveform feature extraction, the waveform may be assessed for artifact or arrhythmia. If artifact or arrhythmia are detected, no prediction of aneurysm size or classification may be outputted.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

With reference to FIG. 7, the present disclosure also relates to a point-of-care device 70 which can be used to screen for and/or monitor aortic aneurysms in a patient. In an example implementation, the point-of-care device is comprised generally of a signal processor 73, a computer memory 74 and one or more user interfaces 75, such as a key pad, a touchscreen, a display, etc. The point-of-care device 70 also include one or more sensors. In one embodiment, the sensor is a PPG sensor 71. In another embodiment, the sensor is an accelerometer 72. In a third embodiment, the sensor is both a PPG sensor 71 and accelerometer 72. Other types of sensors can also be used to measure an arterial waveform of the subject within the scope of this disclosure. It is to be understood that only the relevant components of the device are discussed in relation to FIG. 7, but that other components may be needed to control and manage the overall operation of the device.

During operation, the sensor(s) 71, 72 are configured to measure at least one arterial waveform in the subject; whereas, the signal processor 73 implements the signal processing steps describe above. The signal processor 73 may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various general-purpose systems may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of screening for aortic aneurysms in a subject, comprising:
    measuring, by a sensor, at least one arterial waveform in a subject;
    measuring blood pressure of the subject;
    extracting, by a signal processor, pulse wave velocity from the at least one arterial waveform;
    dividing, by the signal processor, the pulse wave velocity by the blood pressure; and
    detecting, by the signal processor, presence of an aortic aneurysm in the subject in response to a quotient of the pulse wave velocity divided by the blood pressure being less than a threshold.

2. The method of claim 1 wherein measuring at least one arterial waveform comprises measuring a waveform indicative of blood volume using a photo-plethysmography (PPG) sensor.

3. The method of claim 1 wherein measuring at least one arterial waveform comprises measuring a ballistocardiography waveform using an accelerometer or a weighing scale.

4. The method of claim 1 further comprises measuring at least one arterial waveform using a sensor residing in a mobile phone.

5. The method of claim 1 further comprises imaging the aortic aneurysm in the subject using an imaging device, where the imaging is in response to the step of detecting the aortic aneurysm using the extracted features.

6. A method of screening for aortic aneurysms in a subject, comprising:
    measuring, by a sensor, at least one arterial waveform in a carotid artery of the subject;
    determining a first feature from the at least one arterial waveform, where the first feature is indicative of shape of the at least one arterial waveform during an upstroke of the at least one arterial waveform;
    identifying an intersection of two lines fitted to an upstroke of the at least one arterial waveform, determining a first value measured between a peak of the at least one arterial waveform and the intersection;

determining a second value measured between the peak of the at least one arterial waveform and the minimum of the at least one arterial waveform;

computing a ratio of the first value to the second value; and detecting an aortic aneurysm in the subject in response to the ratio being greater than a threshold.

7. A point-of-care device comprising:

a sensor configured to measure an arterial waveform in a subject;

a pressure sensor configured to measure blood pressure of the subject;

a signal processor in data communication with the sensor and the pressure sensor, wherein the signal processor operates to extract pulse wave velocity from the arterial waveform; divide the pulse wave velocity by the blood pressure; and detect presence of an aortic aneurysm in the subject in response to a quotient of the pulse wave velocity divided by the blood pressure being less than a threshold; and an output in data communication with the signal processor and operable to provide an indicator for the aortic aneurysm.

8. The point-of-care device of claim 7 wherein the sensor is further defined as a photo-plethysmography (PPG) sensor.

* * * * *